(12) United States Patent
Tuscher et al.

(10) Patent No.: US 10,292,574 B2
(45) Date of Patent: May 21, 2019

(54) OBLIQUE-VIEW ENDOSCOPE OBJECTIVE

(71) Applicant: Scholly Fiberoptic GmbH, Denzlingen (DE)

(72) Inventors: Jonas Tuscher, Freiburg (DE); Florian Wirth, Biebertal (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 0 days.

(21) Appl. No.: 15/672,745

(22) Filed: Aug. 9, 2017

(65) Prior Publication Data
US 2018/0055341 A1    Mar. 1, 2018

(30) Foreign Application Priority Data

Aug. 24, 2016  (DE) .................. 10 2016 010 296

(51) Int. Cl.
| | |
|---|---|
| *A61B 1/00* | (2006.01) |
| *G02B 23/24* | (2006.01) |
| *A61B 1/055* | (2006.01) |
| *G02B 5/04* | (2006.01) |

(52) U.S. Cl.
CPC ...... *A61B 1/00096* (2013.01); *A61B 1/00179* (2013.01); *A61B 1/055* (2013.01); *G02B 23/243* (2013.01); *G02B 5/04* (2013.01)

(58) Field of Classification Search
CPC . A61B 1/00096; A61B 1/00179; A61B 1/055; G02B 5/04; G02B 23/243
USPC .................. 359/434, 833, 834; 385/115–119
See application file for complete search history.

(56) References Cited

U.S. PATENT DOCUMENTS

| | | | | |
|---|---|---|---|---|
| 4,138,192 | A | | 2/1979 | Yamasita |
| 4,815,833 | A | * | 3/1989 | Zobel ................... G02B 23/243 359/726 |
| 4,846,154 | A | * | 7/1989 | MacAnally ........ A61B 1/00165 600/171 |
| 5,573,493 | A | * | 11/1996 | Sauer ................. A61B 1/00101 600/121 |
| 5,861,987 | A | | 1/1999 | Nakamura et al. |
| 5,892,630 | A | * | 4/1999 | Broome ............ G02B 23/2423 359/656 |
| 6,635,010 | B1 | * | 10/2003 | Lederer ................ G02B 23/243 600/171 |
| 7,280,283 | B1 | | 10/2007 | Kasai |
| 9,474,439 | B2 | | 10/2016 | Baumann et al. |
| 2009/0102961 | A1 | | 4/2009 | Uzawa |
| 2010/0208372 | A1 | * | 8/2010 | Heimer ..................... G01J 3/02 359/834 |

(Continued)

FOREIGN PATENT DOCUMENTS

DE    102012110905    5/2014

*Primary Examiner* — Frank G Font
(74) *Attorney, Agent, or Firm* — Volpe and Koenig, P.C.

(57) ABSTRACT

In the case of an objective arrangement (1) having a deflection unit (4) which guides an imaging beam path (9) from a light entrance (2) to a light exit (3) via a first reflection surface (6) and a second reflection surface (7), it is provided to embody a region (8) of total internal reflection at least in the second reflection surface (7), with this region being configured for total internal reflection in the imaging beam path (9) and this region forming part of a transmission region (5) that is disposed upstream of the first reflection surface (6), through which imaging rays from the light entrance (2) are incident on the first reflection surface (6).

19 Claims, 1 Drawing Sheet

(56) References Cited

U.S. PATENT DOCUMENTS

2014/0071400 A1\* 3/2014 Gao ............... A61B 3/113
351/210
2015/0034802 A1\* 2/2015 Haigis ............ G02B 23/2415
250/208.1

\* cited by examiner

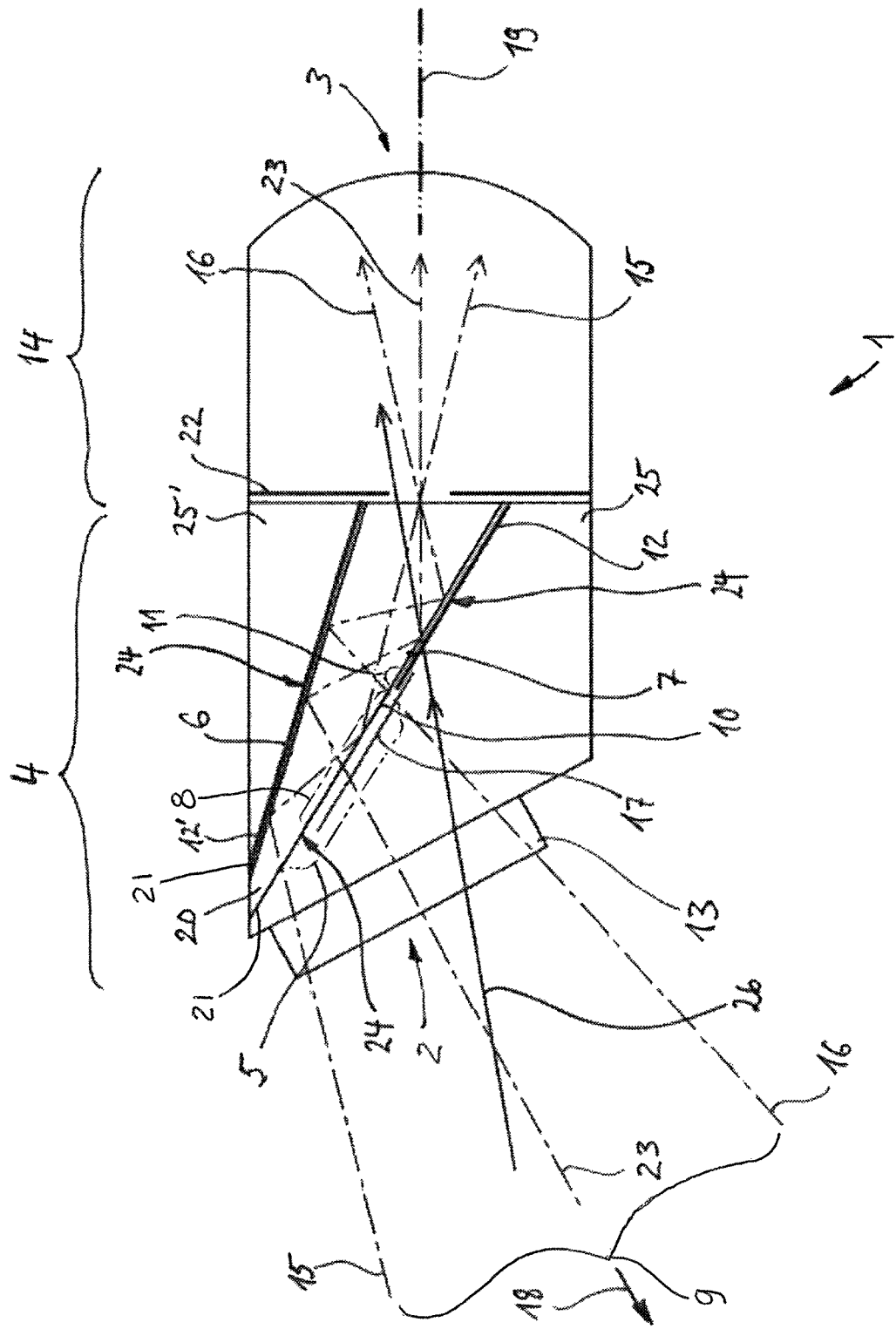

OBLIQUE-VIEW ENDOSCOPE OBJECTIVE

INCORPORATION BY REFERENCE

The following documents are incorporated herein by reference as if fully set forth: German Patent Application No. 10 2016 010 296.9, filed Aug. 24, 2016.

BACKGROUND

The invention relates to an objective arrangement for an endoscope comprising a light exit that is angled in relation to a light entrance and comprising a deflection unit which guides an imaging beam path proceeding from the light entrance to the light exit. Here, the imaging beam path, in particular the marginal rays of the imaging beam path, defines a transmission region, a first reflection surface, and a second reflection surface within the deflection unit. If the imaging beam path is followed through the objective arrangement proceeding from the light entrance, said imaging beam path initially passes through the transmission region in order to be respectively reflected subsequently at the first reflection surface and, thereafter, at the second reflection surface. Consequently, the imaging beam path finally emerges at the light exit of the objective arrangement.

Such objective arrangements are known and used, for example, in endoscopes for imaging an object field which is angled in relation to a shaft axis of the endoscope such that the viewing direction on the object field extends at an angle of e.g. approximately 30° in relation to a longitudinal axis of the endoscope. Here, the endoscope can be embodied either as an endoscope, for example with a relay-lens system, eyepiece lens system or an attached optical fiber bundle, or else as a video endoscope with an integrated image sensor, the latter for example arranged at the distal end of the endoscope (a so-called "chip-in-tip endoscope").

For the purposes of the beam deflection, the deflection unit in the objective arrangement in such endoscopes is typically embodied with two reflection planes, wherein the reflection planes may be arranged parallel to one another or in a manner extending in a convergent fashion and wherein reflection surfaces are embodied in the reflection planes.

Thus, known objective arrangements are often configured in such a way that the incident light initially passes through a first reflection plane in a transmission region in order subsequently to be reflected at a second reflection plane in a first reflection surface. Subsequently, the light that was reflected by the first reflection surface experiences a second reflection in a second reflection surface at a side of the first reflection plane that is facing away from the original direction of incidence of the light. Additionally, objective arrangements in which more than two reflections are used for the beam deflection are also known.

Until now, it has been conventional to embody the respective reflection surfaces on the reflection planes completely by reflective coatings in order to securely steer the light into a downstream image-side optical unit.

SUMMARY

The invention is based on the object of providing a compact deflection unit for an objective arrangement of an endoscope.

In order to achieve this object, an objective arrangement with one or more features of the invention is provided. In particular, according to the invention, in order to achieve the object in an objective arrangement of the type set forth at the outset, it is thus provided that the second reflection surface has a region of total internal reflection which, at least in part, is arranged in the transmission region and which is configured for the total internal reflection of imaging rays.

Here, for example, the region of total internal reflection can be characterized as a region in which imaging rays are deflected by total internal reflection. By way of example, an imaging ray can be understood to mean a light ray which follows the imaging beam path within the objective arrangement and/or which is guided through the objective arrangement for the purposes of imaging. Extraneous rays, which are likewise incident into the objective arrangement through the light entrance but which do not supply any desired contribution to the imaging, for example because they emanate not from an object to be imaged but from stray light or disturbance light sources, can be distinguished therefrom.

Consequently, according to the invention and unlike in the prior art, not all imaging rays are deflected at the second reflection surface by reflective coatings, but some of the imaging rays are deflected by total internal reflection. The advantage of using the total internal reflection instead of a reflective coating for the purposes of the ray deflection lies in the fact that the second reflection surface may overlap with the transmission region. Consequently, it is possible both to transmit light that is incident into the objective arrangement and to subject light emanating from the first reflection surface to total internal reflection at the second reflection surface in this overlap region. The functional two-fold use of the overlap area connected therewith facilitates a reduction in the installation size of the deflection unit. In particular, a distance between the first reflection surface and the second reflection surface can be reduced without restricting a predetermined visual field by reflective coatings since the reflective coatings can be designed with a smaller area on account of using the total internal reflection. The structural limitations which emerge from the use of the previously conventional fully reflectively coated reflection surfaces can therefore be undershot.

Thus, according to the invention, the first reflection surface and the second reflection surface can be aligned relative to one another and the reflective coating in the second reflection plane can be arranged in such a way that a part of the imaging beam path that is transmitted through the transmission region and a part of the imaging beam path that emanates from the first reflection surface and is reflected by the second reflection surface overlap.

Moreover, according to the invention, the reflection surfaces can be embodied in reflection planes, as is known from the prior art, in particular wherein the first reflection surface may be embodied in a first reflection plane and/or the second reflection surface may be embodied in a second reflection plane, in particular together with the transmission region. Alternatively, or in a complementary manner, the first reflection surface and/or the second reflection surface and/or the transmission region may also have a curved configuration. In particular, this allows the design of surfaces with an optical refractive power.

In particular, the invention has identified that, in many applications, the largest field angle that is still imageable is restricted by the dimensions of reflective coatings that are typically formed in the second reflection surface, and that, consequently, a reduction of the reflectively coated surface on the second reflection plane works against this field restriction. Therefore, the inventive concept can also be described as a second reflection surface at the deflection unit being configured for deflecting an imaging beam path partly by means of total internal reflection and partly by means of reflection at a reflective coating, wherein the reflective coating, in particular, covers those regions in which a total internal reflection of the imaging beam path is physically impossible.

In summary, an objective arrangement with a deflection unit that is configured according to the invention offers the advantage of it being possible to deflect the beam paths with large field angles, wherein, at the same time, the deflection unit, and hence the entire objective arrangement, may have a very compact configuration. In particular, in many applications, the invention renders it possible that the external diameter of the objective arrangement does not exceed that of optical units disposed upstream and/or downstream thereof, and so an installation size predetermined by these optical units can be observed within the endoscope tip.

According to the invention, the object can also be achieved by further advantageous embodiments as described below and in the claims.

In an advantageous configuration, provision can be made for the region of total internal reflection not to be reflectively coated. Further, provision can also be made for the region of total internal reflection to form an optical interface at which imaging rays are deflectable by means of total internal reflection. Hence, specific embodiments which facilitate a functional twofold use of the overlap region for both transmitting and reflecting a part of the imaging beam path are specified.

A further advantageous configuration of the invention provides for the first reflection surface to have a wholly or partly reflectively coated embodiment. Hence, an optical interface that is configured for the total internal reflection of imaging rays may also be formed at the first reflection surface. Thus, imaging rays at the second reflection surface can be deflected only by means of a reflective coating and/or by total internal reflection and/or both by total internal reflection and by a partial reflective coating.

According to the invention, the second reflection surface can be configured in such a way that it is wholly or partly reflectively coated outside of the transmission region. In a complementary manner, or alternatively, provision can also be made for the second reflection surface not to have a reflectively coated embodiment within the transmission region. Here, in particular, a region of the second reflection surface that adjoins the transmission region can have a not reflectively coated embodiment outside of the transmission region. In particular, as a result of this configuration, it is possible in particular to avoid the situation where a reflective coating that is embodied in the second reflection surface projects into the transmission region due to manufacturing tolerances and causes unwanted light shadowing there, the latter possibly being expressed as a trim to the visual field. Moreover, it is particularly preferable for a further region of the second reflection surface to have a reflectively coated embodiment outside of the transmission region. This is because, therewith, the second reflection surface can also reflect those imaging rays which just can no longer be deflected by means of total internal reflection, for example on account of an angle of incidence at the second reflection surface that is too small in relation to the normal of the second reflection surface.

A further advantage of a partial reflective coating of the second reflection surface according to the invention can be considered that of being able to effectively prevent stray light and ghost images as may arise, in particular, in the case of only using a total internal reflection for the beam deflection. This is because the partial reflective coating can prevent extraneous light that is incident through the light entrance or through an object-side optical unit from directly entering into an image-side optical unit.

In summary, the second reflection surface may therefore, according to the invention, be subdivided into a not reflectively coated partial surface and a reflectively coated partial surface, with the not reflectively coated partial surface forming an optical interface for the total internal reflection of imaging rays. Here, in particular, the not reflectively coated partial surface can cover the transmission range. In particular, it is advantageous if, in the process, the not reflectively coated partial surface extends beyond the transmission region for the aforementioned reasons.

In a further configuration of the objective arrangement according to the invention, provision can be made for at least 10%, preferably at least 20%, particularly preferably at least 30%, in particular at least 40%, of the second reflection surface to have a not reflectively coated embodiment and/or to be configured for the total internal reflection of imaging rays. As a result of such a configuration, a particularly large overlap between the transmission region and the second reflection surface can be developed, which has a very advantageous effect on the installation size of the deflection unit.

In order to avoid that the not reflectively coated region of the second reflection surface comes to rest in a region of an optical interface in which a total internal reflection is just no longer possible on account of manufacturing tolerances, provision can also be made for a reflectively coated region outside of the transmission region to overlap a region of the second reflection surface in which a total internal reflection of imaging rays would still be possible. What such a configuration can avoid is a situation where imaging rays are no longer deflected at the interface and consequently lost for the imaging as a result of transmission through the interface.

A further, particularly preferred configuration of the second reflection surface provides for a reflectively coated region of the second reflection surface outside of the transmission region to reach up to the points at which imaging rays impinge on the second reflection surface at an angle of incidence that lies 5 degrees above the critical angle of the total internal reflection that is predetermined by the optical interface. Here, the term optical interface refers to that optical interface in which the not reflectively coated region of the second reflection surface lies. As a consequence, the beam path can therefore, according to the invention, be designed in such a way that imaging rays always impinge on a not reflectively coated region of the second reflection surface with an angle of incidence that is 5 degrees above the critical angle of the total internal reflection that is predetermined by this optical interface. Hence, these imaging rays can always be reliably reflected with total internal reflection.

A specific configuration of the objective arrangement according to the invention provides for the deflection unit to be formed by at least two prisms that are cemented to one another by means of an optical adhesive. According to the invention, reflection and transmission surfaces can therefore, in particular, be embodied at contact planes of the prisms. Here, it is preferable if the prisms are each manufactured from an optical glass or plastic. According to the invention, both prisms, in particular, can be penetrated by the imaging beam path.

Furthermore, it can be advantageous if the first reflection surface and the second reflection surface are embodied on outer surfaces of one of the at least two prisms. Hence, both the first reflection and the second reflection may occur at the outer surfaces of a prism such that the imaging beam path only needs to pass an adhesive layer once, namely in the transmission region.

It can further be advantageous if the at least two prisms have the same refractive index. This is because there is, at best, a minimal beam offset in this case, however, no light refraction during the passage through a transmission region with a plane embodiment, said transmission region, in particular, being able to be formed by a cemented interface between the two prisms.

Further, according to the invention, provision can be made for the optical adhesive to have a smaller refractive index than the prism on which the second reflection surface is embodied. In this case, the total internal reflection may occur on the interface of this prism to the optical adhesive, i.e. at the interface to the optically thinner medium. It is advantageous here that the total internal reflection may occur in the second reflection surface without, in the process, imaging rays penetrating into the adhesive layer and experiencing an optical refraction that reduces the angle of incidence prior to the total internal reflection. Consequently, a larger region of the second reflection surface, in which imaging rays impinge with angles of incidence that are sufficiently large for total internal reflection, may remain without a reflective coating, which increases the freedom for the optical design of the deflection body since, in particular, it is possible for the region of total internal reflection to have a larger design. Moreover, it is possible to avoid imaging rays unnecessarily having to pass through the adhesive layer, which typically has a lower transmissivity and optical defects. The optical adhesive can also be used to compensate a layer thickness produced by the reflective coating. In this way, it is possible to continue the adjacent prism, even behind the reflective coating.

For the purposes of efficiently manufacturing the objective arrangement, it may be advantageous if at least one reflectively coated region is formed by means of a reflecting, preferably thin coating. Moreover, this consequently allows the use of a layer thickness of the adhesive layer that is as small as possible, which is advantageous for a high transmission of the deflection unit.

For the objective arrangement, provision can also be made, according to the invention, for the first reflection surface and/or the second reflection surface to coincide with the outer surfaces of a prism, preferably wherein the outer surfaces of the prism are wholly or partly provided with a reflecting, preferably thin coating.

This is because, particularly if both the first reflection surface and the second reflection surface coincide with the outer surfaces of a prism, it is possible to obtain a particularly expedient beam path since a beam offset, as may occur on account of light refractions during the passage through adhesive layers between the prism and adjacent optical components, such as e.g. a further adjacent prism, can be avoided in this case.

A further configuration of the invention provides for the objective arrangement to comprise an object-side optical unit and/or an image-side optical unit. Here, the object-side optical unit can transmit imaging rays into the deflection unit and/or the image-side optical unit can receive imaging rays from the deflection unit. A particularly advantageous configuration of such an objective arrangement provides for the object-side optical unit to comprise a preferably flat concave lens and/or for the image-side optical unit to comprise an aperture stop. As a result of this, the optical performance of the objective arrangement can be substantially increased; by way of example, this provides a particularly simple way of increasing the viewing field or the field angle of the endoscope or adjusting of the aperture angle of the objective arrangement.

A preferred use of the invention provides the arrangement of the objective arrangement according to the invention, in particular as described above and/or as claimed in any one of the claims directed to an objective arrangement, at a distal end of the endoscope.

The invention will now be described in more detail on the basis of exemplary embodiments, without, however, being restricted to these exemplary embodiments.

BRIEF DESCRIPTION OF THE DRAWINGS

Further exemplary embodiments emerge by combining the features of individual claims or of a plurality of claims with one another and/or with individual features or a plurality of features of the respective exemplary embodiment. In particular, it is consequently possible to obtain embodiments of the invention from the subsequent description of a preferred exemplary embodiment in conjunction with the general description, the claims, and the drawings. Shown is:

FIG. 1 which shows a cross section through an objective arrangement that is configured according to the invention and comprises a deflection unit and comprises an image-side optical unit and an object-side optical unit.

DETAILED DESCRIPTION OF THE PREFERRED EMBODIMENTS

FIG. 1 shows an objective arrangement according to the invention that is denoted, as a whole, by 1. The objective arrangement 1 comprises a light entrance 2 which, for example, can be arranged at the distal end of an endoscope that is not presented in any more detail and known per se.

The light entrance 2 captures light from an examination environment and steers this light to an angled light exit 3 in a way that is still to be explained in more detail below. What this angling achieves is that the light entrance 2 is aligned in a different direction than would be predetermined by the light exit 3.

A deflection unit 4 which guides the imaging beam path 9 between the light entrance 2 and the light exit 3 is provided for angling the captured light.

To this end, a transmission region 5 is formed in the deflection unit 4, the boundaries of said transmission region being defined by the incident light rays of the imaging beam path 9.

A first reflection surface 6, at which the imaging beam path 9 is reflected for first time, is embodied downstream of the transmission region 5 in the beam direction of the imaging beam path 9.

A second reflection surface 7, at which the imaging rays of the imaging beam path 9 are reflected a second time, is embodied downstream of the first reflection surface 6 in the imaging direction of the imaging beam path 9.

Subsequently, the imaging beam path 9 is guided through an aperture stop 22 and defines an optical axis of the light exit 3, which is formed by the chief ray 23.

In the same way, the chief ray 23 defines an optical axis of the light entrance 2, which coincides with the viewing direction 18 of the endoscope.

Therefore, the aforementioned angling between the light entrance 2 and the light exit can be characterized, for example, by the angle between the viewing direction 18 of the endoscope and the longitudinal axis 19 of the endoscope, the latter being given by the optical axis of the light exit 3 and coinciding with a direction of extent of a shaft of the endoscope.

According to the invention, a region 8 of total internal reflection is embodied in the second reflection surface 7. This region 8 of total internal reflection is arranged relative to the imaging beam path 9 in such a way that total internal reflection occurs in the imaging beam path 9 within the region 8 of total internal reflection. To this end, the outside environment of the second reflection surface 7 as an interface 10 is chosen accordingly, depending on a refractive index in the imaging beam path 9.

The region 8 of total internal reflection overlaps with the transmission region 5, as can be seen from the plotted sites of reflection of the left marginal ray 15.

In general, it is possible to state that the imaging beam path 9 in FIG. 1 is indicated by the left marginal ray 15, the right marginal ray 16, and the chief ray 23.

On the rear side, the first reflection surface 6 is completely reflectively coated as indicated at 12' in order to ensure that the incident light rays are reflected.

The second reflection surface 7 is completely reflectively coated outside of the transmission region 5. Therefore, the reflective coating projects up to the boundary of the transmission region 5 in order thus to mask extraneous rays 26.

Within the transmission region 5, the second reflection surface 7 has a not reflectively coated embodiment and therefore presents no irradiation obstacle for the light rays that are incident from the object-side optical unit 13.

Here, the angle conditions in the imaging beam path 9 are selected in such a way that an adjacent region 11 of the second reflection surface 7, in which total internal reflections may likewise take place, is formed outside of the transmission region 5 and hence within the reflectively coated region of the second reflection surface 7. This region 8 of total internal reflection therefore forms the region of possible total internal reflection 17 together with the adjacent region 11.

Hence, a reflective coating is not required in the adjacent region 11. However, in the present exemplary embodiment, this adjacent region 11 likewise has a reflectively coated embodiment in order to ensure that a reflection also takes place there in any case. A further region 12, adjoining this, of the second reflection surface 7 has a reflectively coated embodiment in any case in order, in particular, to reflect the right marginal ray 16, the angle of incidence of which at the second reflection surface 7 would not permit total internal reflection.

Hence, the reflectively coated region 12 has such a large embodiment that it overlaps with, and covers, the adjacent region 11, in which a total internal reflection of imaging rays would still be possible.

The deflection unit 4 comprises a prism 20, on which the first reflection surface 6 and—opposite thereto—the second reflection surface 7 with the transmission region 5 are formed. Here, the reflection surfaces 6, 7 and the transmission region 5 are formed on the outer surfaces 21 of the prism 20.

Adjacent prisms 25, 25' which are respectively placed onto the reflection surface 6, 7, are provided for this prism 20. Here, the prisms 20, 25, 25' are cemented to one another by an optical adhesive 24.

The prisms 20, 25, 25' may each be formed of e.g. optical glass or plastic. It is particularly expedient if the prisms 20, 25, 25', which guide the imaging beam path 9, are manufactured from materials with corresponding refractive indices. The optical adhesive 24 has a lower refractive index than the prism 20 which forms the second reflection surface 7. This facilitates the formation of a region 8 of total internal reflection at the optical interface 10.

The aforementioned reflective coatings are applied by way of a reflective coating onto the prism 20.

The reflection surfaces 6, 7 that are embodied here as planes in the exemplary embodiment have a widening profile in the beam path.

During use, the objective arrangement 1 according to the invention is provided with an object-side optical unit 13 at the light entrance and with an image-side optical unit 14 at a light exit.

Consequently, the object-side optical unit 13 transmits the imaging rays into the deflection unit 4, while the image-side optical unit 14 receives the imaging rays, which have been deflected at least twice, from the deflection unit 4.

To this end, provision can be made for the object-side optical unit 13 to comprise a plano-concave lens and for the image-side optical unit 14 to comprise an aperture stop.

In the case of the objective arrangement 1 comprising a deflection unit 4 which guides an imaging beam path 9 from a light entrance 2 to a light exit 3 via a first reflection surface 6 and a second reflection surface 7, it is provided to embody a region 8 of total internal reflection at least in the second reflection surface 7, said region being configured for total internal reflection in the imaging beam path 9 and said region forming part of a transmission region 5 that is disposed upstream of the first reflection surface 6, through which imaging rays from the light entrance 2 are incident on the first reflection surface 6.

LIST OF REFERENCE SIGNS

1 Objective arrangement
2 Light entrance
3 Light exit
4 Deflection unit
5 Transmission region
6 First reflection surface
7 Second reflection surface
8 Region of total internal reflection
9 Imaging beam path
10 Optical interface
11 Adjoining region
12, 12' Reflectively coated region
13 Object-side optical unit
14 Image-side optical unit
15 Left marginal ray
16 Right marginal ray
17 Region of possible total internal reflection
18 Viewing direction of the endoscope
19 Longitudinal axis of the endoscope
20 Prism
21 Outer surface
22 Aperture stop
23 Chief ray
24 Optical adhesive
25, 25' Adjacent prism
26 Extraneous ray

The invention claimed is:

1. An objective arrangement (1) for an endoscope comprising:
   a light exit (3) that is angled in relation to a light entrance (2);
   a deflection unit (4) which guides an imaging beam path (9) proceeding from the light entrance (2) to the light exit (3), the deflection unit (4) includes a transmission region (5), a first reflection surface (6), and a second reflection surface (7) located along the imaging beam path (9) such that captured images are adapted to pass along the imaging beam path (9) through the transmission region (5) for reflection at the first reflection surface (6) and further reflection at the second reflection surface (7);

the transmission region (5) extends through a portion of the second reflection surface (7), and the second reflection surface (7) has a region (8) of total internal reflection arranged at least in part in the transmission region (5) and which is configured for total internal reflection of imaging rays; and the first reflection surface (6) is at least partly reflectively coated.

2. The objective arrangement as claimed in claim 1, wherein the region (8) of total internal reflection is not reflectively coated and forms an optical interface (10) at which the imaging rays are deflectable by total internal reflection.

3. The objective arrangement (1) as claimed in claim 1, wherein the second reflection surface (7) is not reflectively coated within the transmission region (5), and includes a region (11) of the second reflection surface (7) that adjoins the transmission region (5) that is not reflectively coated outside of the transmission region (5).

4. The objective arrangement as claimed in claim 1, wherein the second reflection surface (7) is not reflectively coated within the transmission region (5), and the first reflection surface (6) being at least partly reflectively coated comprises a further region (12) of the second reflection surface (7) that is reflectively coated.

5. The objective arrangement (1) as claimed in claim 1, wherein at least 10% of the second reflection surface (7) is not reflectively coated.

6. The objective arrangement (1) as claimed in claim 1, wherein the first reflection surface (6) being at least partly reflectively coated comprises a reflectively coated region (12) that overlaps a region of the second reflection surface (7) outside of the transmission region (5), and the reflectively coated region (12) is adapted for a total internal reflection of the imaging rays.

7. The objective arrangement (1) as claimed in claim 1, wherein the first reflection surface (6) being at least partly reflectively coated comprises a reflectively coated region (12) of the second reflection surface (7) outside of the transmission region (5).

8. The objective arrangement (1) as claimed in claim 7, wherein the reflectively coated region (12) comprises a reflective coating.

9. The objective arrangement as claimed in claim 1, wherein the deflection unit (4) comprises at least two prisms (20, 25) that are cemented to one another by an optical adhesive (24).

10. The objective arrangement as claimed in claim 9, wherein the first reflection surface (6) and the second reflection surface (7) are embodied on outer surfaces (21) of one of the at least two prisms (20, 25).

11. The objective arrangement as claimed in claim 9, wherein the imaging beam path (9) is defined through the prisms (20, 25).

12. The objective arrangement as claimed in claim 9, wherein the prisms (20, 25) have a same refractive index, and the optical adhesive (24) has a smaller refractive index than the prism (20) on which the second reflection surface (7) is embodied.

13. The objective arrangement (1) as claimed in claim 1, wherein at least one of the first reflection surface (6) or the second reflection surface (7) coincide with outer surfaces (21) of a prism (20), and the outer surfaces (21) of the prism (20) are at least partly provided with a reflective thin coating.

14. The objective arrangement (1) as claimed in claim 1, further comprising an object-side optical unit (13) through which imaging rays are adapted to pass into the deflection unit (4).

15. The objective arrangement (1) as claimed in claim 1, further comprising an image-side optical unit (14) that is adapted to receive the imaging rays from the deflection unit (4).

16. The objective arrangement (1) as claimed in claim 15, wherein the object-side optical unit (13) comprises a concave lens, or the image-side optical unit (14) comprises an aperture stop, or both.

17. An endoscope comprising an objective arrangement (1) as claimed in claim 1 located at a distal end thereof.

18. The objective arrangement (1) as claimed in claim 1, wherein at least 10% of the second reflection surface (7) is configured for the total internal reflection of imaging rays.

19. An objective arrangement (1) for an endoscope comprising:

a light exit (3) that is angled in relation to a light entrance (2);

a deflection unit (4) which guides an imaging beam path (9) proceeding from the light entrance (2) to the light exit (3), the deflection unit (4) includes a transmission region (5), a first reflection surface (6), and a second reflection surface (7) located along the imaging beam path (9) such that captured images are adapted to pass along the imaging beam path (9) through the transmission region (5) for reflection at the first reflection surface (6) and further reflection at the second reflection surface (7);

the transmission region (5) extends through a portion of the second reflection surface (7), and the second reflection surface (7) has a region (8) of total internal reflection arranged at least in part in the transmission region (5) and which is configured for total internal reflection of imaging rays; and the second reflection surface (7) is at least partly reflectively coated outside of the transmission region (5).

* * * * *